US009149588B2

(12) United States Patent
Gordon et al.

(10) Patent No.: US 9,149,588 B2
(45) Date of Patent: Oct. 6, 2015

(54) SYSTEMS AND METHODS FOR DRIVING SEALED NEBULIZERS

(75) Inventors: Benjamin Morris Gordon, Cambridge (GB); Steven David Gardner, Yaxley (GB); Matthew James Hayes, Cambridge (GB)

(73) Assignee: NEKTAR THERAPEUTICS, San Carlos, CA (US)

( * ) Notice: Subject to any disclaimer, the term of this patent is extended or adjusted under 35 U.S.C. 154(b) by 716 days.

(21) Appl. No.: 13/384,579

(22) PCT Filed: Jul. 19, 2010

(86) PCT No.: PCT/US2010/042473
§ 371 (c)(1),
(2), (4) Date: Jan. 17, 2012

(87) PCT Pub. No.: WO2011/009133
PCT Pub. Date: Jan. 20, 2011

(65) Prior Publication Data
US 2012/0111963 A1 May 10, 2012

Related U.S. Application Data

(60) Provisional application No. 61/226,591, filed on Jul. 17, 2009.

(51) Int. Cl.
*A61M 15/00* (2006.01)
*A61M 11/00* (2006.01)
(Continued)

(52) U.S. Cl.
CPC ......... *A61M 15/0085* (2013.01); *A61M 11/005* (2013.01); *A61M 16/0833* (2014.02);
(Continued)

(58) Field of Classification Search
CPC .......... A61M 11/005; A61M 15/0085; A61M 16/14; A61M 2016/0024; A61M 16/0833; A61M 2205/8206; B05B 17/0646
USPC ............................ 239/102.1, 102.2; 700/280
See application file for complete search history.

(56) References Cited

U.S. PATENT DOCUMENTS 3,819,961 A 6/1974 Verlet et al.
5,349,852 A 9/1994 Kamen et al.
(Continued)

FOREIGN PATENT DOCUMENTS

JP H05-261324 A 10/1993
TW I294791 3/2008

OTHER PUBLICATIONS

Office Action in related Eurasian application 201200134 issued on Apr. 24, 2014, 3 pages.

(Continued)

*Primary Examiner* — Jason Boeckmann
(74) *Attorney, Agent, or Firm* — Kilpatrick Townsend Stockton LLP

(57) ABSTRACT

Various methods, devices, and systems are described for aerosolizing a liquid. Embodiments may include sealing the liquid within a reservoir. An output waveform signal may be generated. A nebulizer element may be vibrated to aerosolize the liquid. A negative pressure may be produced within the reservoir as the liquid is aerosolized. The output waveform signal may cause the nebulizer element to vibrate. Embodiments may involve determining a phase shift between a current of the output waveform signal and a voltage of the output waveform signal. Also, embodiments may involve adjusting a frequency of the output waveform signal at least partially based on the phase shift. Further, embodiments may involve adjusting the voltage of the output waveform signal at least partially based on the frequency of the output waveform signal.

19 Claims, 8 Drawing Sheets

(51) Int. Cl.
*A61M 16/14* (2006.01)
*A61M 16/08* (2006.01)
*B05B 17/00* (2006.01)
*A61M 16/00* (2006.01)

(52) U.S. Cl.
CPC ............ *A61M16/14* (2013.01); *B05B 17/0646* (2013.01); *A61M 16/0066* (2013.01); *A61M 2016/0024* (2013.01); *A61M 2205/8206* (2013.01)

(56) References Cited

U.S. PATENT DOCUMENTS

| | | | |
|---|---|---|---|
| 5,853,665 | A | 12/1998 | Ade et al. |
| 6,569,109 | B2 | 5/2003 | Sakurai et al. |
| 6,978,779 | B2 | 12/2005 | Haveri |
| 6,983,747 | B2 | 1/2006 | Gallem et al. |
| 7,155,980 | B2 | 1/2007 | Kurtz |
| 7,197,948 | B2 | 4/2007 | Sander |
| 2001/0039389 | A1 | 11/2001 | Sakurai et al. |
| 2002/0129813 | A1 | 9/2002 | Litherland et al. |
| 2003/0196660 | A1 | 10/2003 | Haveri |
| 2005/0224076 | A1 | 10/2005 | Pfichner et al. |
| 2006/0102172 | A1 | 5/2006 | Feiner et al. |
| 2007/0015281 | A1 | 1/2007 | Bebee |
| 2007/0152081 | A1 | 7/2007 | Chou et al. |

OTHER PUBLICATIONS

International Search Report and Written Opinion of PCT/US2010/042473 mailed on Sep. 15, 2010, 11 pages.
Extended European Search Report of PCT/US2010/042473 mailed on Aug. 28, 2014, 17 pages.
Office action in Chinese Application No. 201080036580 issued on Jun. 13, 2014. 5 pages.
International Search Report and Written Opinion of related PCT/US2013/058004 mailed on Jul. 7, 2014, 141 pages.
Office action in Japanese Application No. 553851 issued on Jul. 15, 2014, 3 pages.
Office action in Mexican Application No. 553853 issued on Jul. 7, 2014, 2 pages.
Eurasian Office Action mailed on Oct. 30, 2014 for Eurasian Application No. 201200134 filed on Jul. 19, 2010, all pages.
Chinese Office Action mailed on Oct. 31, 2014 for Chinese Application No. 201080036580.X filed on Jul. 19, 2010, all pages.
Australian Office Action mailed on Nov. 27, 2014 for Australian Application No. 2010273957 filed on Jul. 19, 2010, all pages.
Israeli Office Action mailed on Dec. 4, 2014 for Israeli Application No. 217512 filed on Jul. 19, 2010, all pages.

SYSTEMS AND METHODS FOR DRIVING SEALED NEBULIZERS

CROSS-REFERENCES TO RELATED APPLICATIONS

This Application claims the benefit of U.S. Provisional Patent Application No. 61/226,591, filed Jul. 17, 2009 entitled SYSTEMS AND METHODS FOR DRIVING SEALED NEBULIZERS, and is related to Provisional Patent Application No. 61/226,567, filed Jul. 17, 2009 entitled NEGATIVELY BIASED SEALED NEBULIZERS SYSTEMS AND METHODS, the entire disclosures of which is incorporated by reference for all purposes.

BACKGROUND OF THE INVENTION

Embodiments of the present invention relate to nebulizers. In particular, the present invention relates to use of a variable voltage and frequency driver for at nebulizer having a sealed liquid drug reservoir capable of maintaining a negative internal bias pressure.

A wide variety of procedures have been proposed to deliver a drug to a patient. In some drag delivery procedures the drag is a liquid and is dispensed in the form of fine liquid droplets for inhalation by a patient. A patient may inhale the drug for absorption through lung tissue. Further, the droplets forming the atomized mist may need to be very small to travel through small airways of the lungs. Such a mist may be formed by a nebulizer.

SUMMARY

Various systems, methods, and devices are described for driving a nebulizer using a driver unit The nebulizer may include a sealed drug reservoir such that a negative bias pressure may form within the drug reservoir as liquid is drained from it. As the negative bias pressure changes, the resonant frequency of the nebulizer element may change. A driver may be used to drive the nebulizer element and cause it to vibrate. The driver may output a waveform, signal of varying frequency and magnitude to the nebulizer such that the nebulizer element vibrates at or near a resonant frequency and the nebulizer element atomizes liquid at a constant or near constant rate and droplet size.

In some embodiments, a method for determining a resonant frequency of an element of a nebulizer with a negatively biased liquid reservoir is described. The method may include driving a nebulizer using an electrical signal, the electrical signal comprising a current and a voltage. The method may include measuring a phase shift between the voltage and the current of the electrical signal driving the nebulizer. The method may also include, based at least in part on the phase shift of the electrical signal driving, the nebulizer, determining, a resonant frequency of the element of the nebulizer.

In some embodiments, the method former comprises based at least in part on the resonant frequency of the nebulizer determined by the driver, determining, a voltage magnitude for the electrical signal. In some embodiments, the negatively biased liquid reservoir causes the resonant frequency of the element of the nebulizer to vary as liquid is drained from the negatively biased liquid reservoir. In some embodiments, the electrical signal driving the nebulizer causes the element of the nebulizer to vibrate and atomize liquid stored in the negatively biased liquid reservoir. In some embodiments, the method further comprises based at least in part on the resonant frequency of the nebulizer determined by the driver, determining, by the driver, a negative bias pressure within the negatively biased liquid reservoir of the nebulizer. In some embodiments, the method further comprises adjusting the frequency of the electrical signal to the nebulizer, wherein a roughly constant phase shift is maintained between the voltage and current of the electrical signal. In some embodiments, the voltage magnitude is determined using a stored set of values, and the stored set of values vary depending on a liquid in the negatively biased liquid reservoir.

In some embodiments, a device for driving an element of a nebulizer is present. The device may include an amplifier, configured to generate an output waveform signal, the output waveform signal comprising an output current and an output voltage, wherein the output waveform signal drives the element of the nebulizer at the output frequency. The device may include a phase shift detector, configured to determine the phase shift between the output current and the output voltage of the output waveform signal. The device may include a resonant frequency tracker, configured to generate a waveform signal of a variable frequency input to the amplifier, wherein the variable frequency is adjusted based on the phase shift of the output waveform signal determined by fee phase shift detector module. The device may include a voltage profile, configured to adjust the output voltage of the output waveform signal output by the amplifier based on the frequency of the waveform signal generated by the resonant frequency tracker.

In some embodiments, a system for atomizing liquid stored in a negatively bias pressured liquid reservoir may be present. The system may include a nebulizer, comprising an element and the negatively bias pressured liquid reservoir. The element may be configured to vibrate to atomize liquid drained from the negatively bias pressured liquid reservoir. A negative bias pressure of the negatively bias pressured reservoir may change as liquid stored in the negatively bias pressured liquid-reservoir is drained. The negatively bias pressured reservoir may be sealed such that air from the external environment substantially does not enter the negatively bias pressured reservoir as liquid stored in the negatively bias pressured liquid reservoir is drained. The system may include a driver. The driver may include a phase shift detector, configured to determine the phase shift between a current of an output waveform signal and a voltage of the output waveform signal. The driver may include a resonant frequency tracker, configured to generate an output waveform that adjusts the frequency of the output waveform signal, wherein the frequency is adjusted based on the phase shift determined by the phase shift detector module. The driver may include a voltage profile, configured to adjust a voltage of the output waveform signal based on the frequency of the output waveform generated by the resonant frequency tracker.

In some embodiments, a method for aerosolizing a liquid is present. The method may include sealing the liquid within a reservoir. The method may also include generating an output waveform signal and vibrating a nebulizer element to aerosolize the liquid. A negative pressure may be produced within the reservoir as the liquid is aerosolized. The output waveform signal may cause the nebulizer element to vibrate. The method may include determining a phase shift between a current of the output waveform, signal and a voltage of the output waveform signal. The method may include adjusting a frequency of the output waveform signal at least partially based on the phase shift. Further, the method may include adjusting the voltage of the output waveform signal at least partially based on the frequency of fee output waveform signal.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following fee reference label by a second label that distinguishes among the similar components. If only the first reference label is used in the specification, the description is applicable to any one of the similar components having fee same first reference label irrespective of the second reference label.

DETAILED DESCRIPTION OF THE INVENTION

Figure 1A:
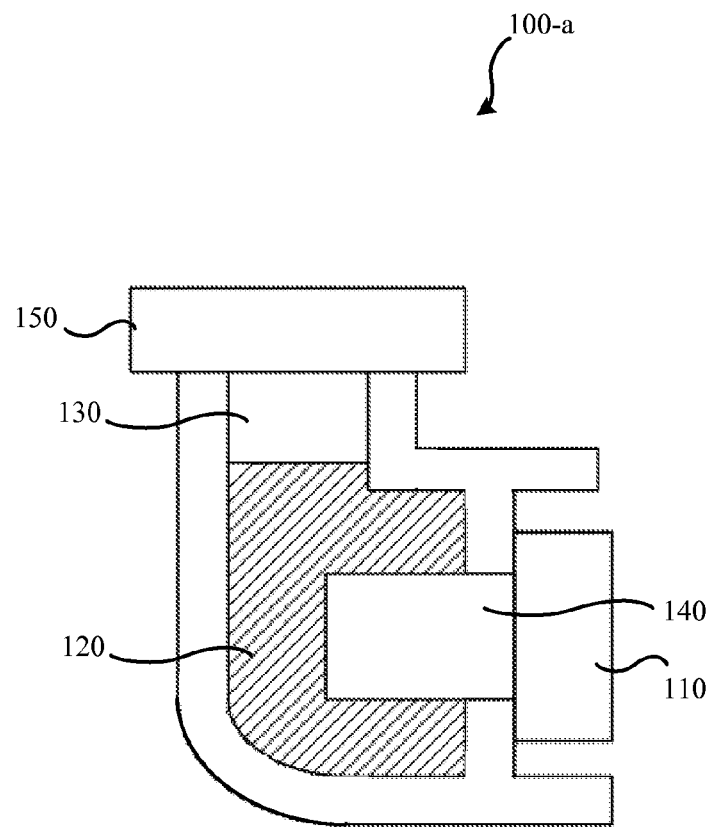
FIG. 1A illustrates a simplified embodiment of a nebulizer.

Devices, systems, and methods are described for the implementation of a novel architecture for driving a nebulizer. The invention provides various ways for driving nebulizers at the nebulizers' resonance frequencies, particularly nebulizers with sealed drug reservoirs capable of developing a negative bias pressure (meaning the pressure within the reservoir is less than the pressure outside of the reservoir) as liquid is evacuated from the drug reservoir.

By creating a negative bias pressure within the drug reservoir of a nebulizer, the efficiency of a nebulizer may be increased, thus allowing it to achieve higher liquid flow rates, with smaller and more consistent droplet sizes, than in comparable conditions without a negative bias pressure. Such a negative bias pressure may be created by sealing the drug reservoir. As the liquid drug is drained from the drug reservoir (with little to no air entering to replace the drug's volume), a negative bias pressure may be created. While the negative bias pressure may assist in maintaining consistently sized droplets of mist, as the negative bias pressure decreases in pressure, the flow rate of liquid from the nebulizer may increase.

An increased flow rate caused by a negative bias pressure may lead to the wrong dose of a medicine being delivered to a patient and/or the generation of improper droplet sizes. Such improper droplet sizes may alter how the droplets are absorbed into the human body. For example, if a patient inhales droplets that are too large, the droplets may not propagate into the deep lung tissue of the patient, but rather, the droplets may gather in the patient's larger airways. This may prevent proper absorption of the droplets by the patient.

The droplets may be created from a stored amount of liquid in the drug reservoir by a nebulizer element. The nebulizer element may be an aperture plate containing a number of small holes. When an electrical signal, such as a waveform, is applied to the nebulizer element, the nebulizer element may vibrate at or near the frequency of the waveform received. While vibrating, the nebulizer element may allow an amount of the liquid to pass through the element and form airborne droplets. The nebulizer element may function more efficiently and produce consistent droplet sizes when the nebulizer element is vibrating at or near its resonant frequency.

However, as the negative bias pressure within the drug reservoir changes (e.g., a greater difference between the pressure inside the drug reservoir and the ambient pressure outside of the drug reservoir is formed) the resonant frequency of the nebulizer element may change. In order to maintain the nebulizer element vibrating at its (current) resonant frequency, it may be necessary to change the frequency of waveform used to drive the nebulizer element.

Therefore, if a negative bias pressure is maintained in the drug reservoir, the frequency and magnitude of the waveform used to drive the nebulizer element needs to vary as the negative bias pressure within the drug reservoir changes in order to maintain efficient operation of the nebulizer element, including maintaining consistent dosing of the liquid drag and consistent droplet sizes.

To be clear, a sealed reservoir refers to a reservoir that prevents air from entering the reservoir as liquid is drained from the drug reservoir. It may, however, still be possible for air to enter the sealed drug reservoir through holes in the nebulizer element. The greater the negative bias pressure (that is, the greater the difference between the pressure of the external environment and the pressure within the drug reservoir) the faster air may enter through the nebulizer element.

FIG. 1A illustrates an embodiment of a possible nebulizer 100-$a$. The nebulizer 100-$a$ may include a nebulizer element 110, a drug reservoir 120, a head space 130, an interface 140, and a cap 150. The nebulizer element 110 may be comprised of a piezoelectric ring that may expand and contract when an electric voltage is applied to the ring. The nebulizer element 110 may be a vibrating aperture plate. The piezoelectric ring may be attached to a perforated membrane. Such a perforated membrane may have a number of holes passing through it. When an electric voltage is applied to the piezoelectric ring, this may cause the membrane to move and/or flex. Such movement of the membrane, while in contact with a liquid may cause the atomization (alternatively referred to as aerosolization) of the liquid.

A supply of a liquid; commonly a liquid drug, may be held in the drug reservoir 120. As illustrated, a drug reservoir is partially filled with a liquid drug. As the liquid drug is atomized, the amount of liquid drug remaining in the drug reservoir 120 may decrease. Depending on the amount of liquid drug in the drug reservoir 120, only a portion of the reservoir may be filled with liquid drug. The remaining portion of the drug reservoir 120 may be filled with gas, such as air. This space is commonly referred to as head space 130. An interface 140 may serve to transfer amounts of liquid drug between the drug reservoir 120 and the nebulizer element 110.

Nebulizers, and the techniques associated with such nebulizers, are described generally in U.S. Pat. Nos. 5,164,740; 5,938,117; 5,586,550; 5,758,637; 6,014,970; 6,085,740; 6,235,177; 6,635,824; 7,322,349 the complete disclosures of which are incorporated by reference for all purposes.

Figure 1B:
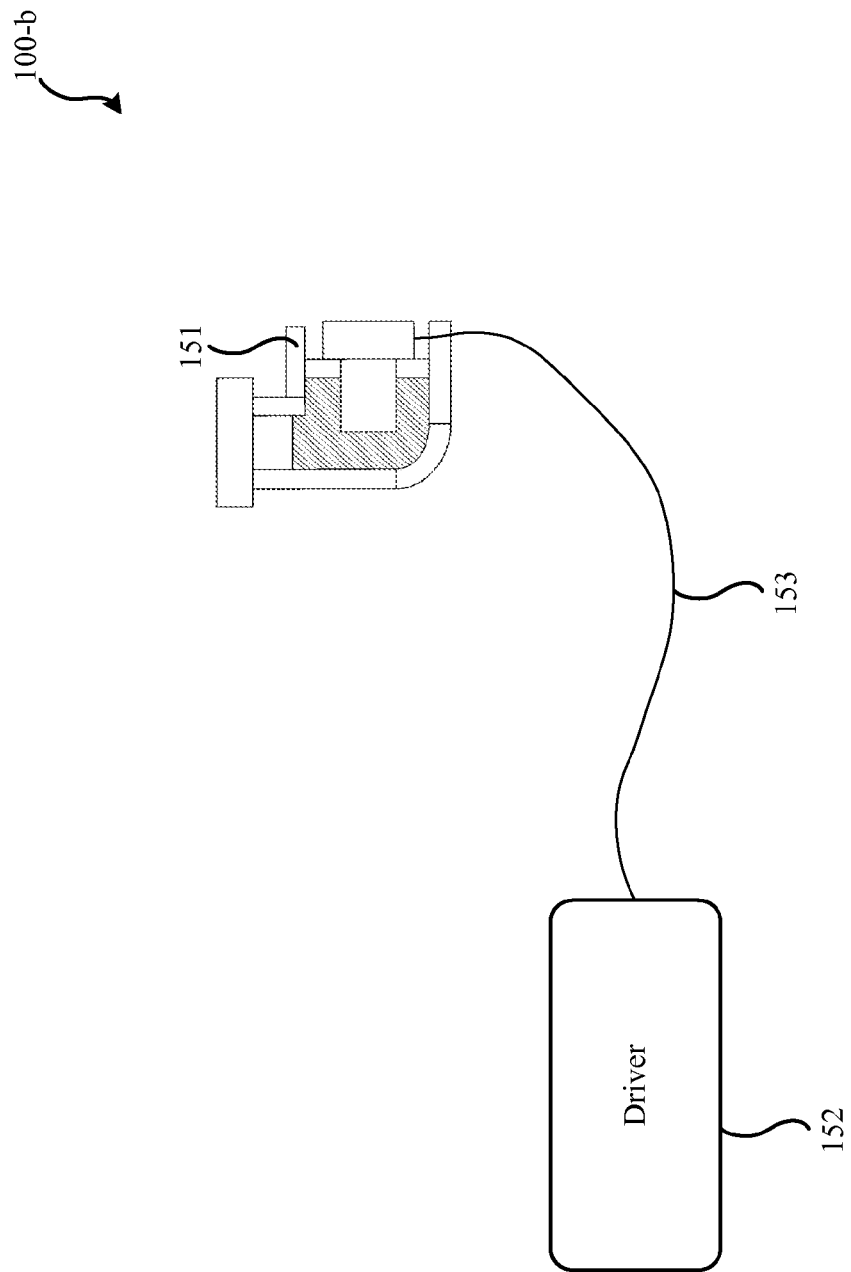
FIG. 1B illustrates a simplified embodiment of a nebulizer with a driver unit.

A nebulizer with a sealed drug reservoir may be part of a larger system. The embodiment of FIG. 1B illustrates such a system 100-$b$. FIG. 1B illustrates a nebulizer 151 with a sealed drag reservoir connected to a driver 152. The sealed nebulizer illustrated in FIG. 1B may be the nebulizer of FIG. 1A, or may represent some other nebulizer. Driver 152 may control the rate and magnitude of vibration of the nebulizer element on nebulizer 151. Driver 152 may be connected to nebulizer element 151 via cable 153. Driver 152 may regulate the voltage and frequency of the signal provided to the nebulizer element of nebulizer 151. The regulation of the voltage and frequency of the signal may he based on the resonant frequency of the nebulizer element of nebulizer 151. Such a signal may vary depending on the magnitude of the negative bias pressure.

Figure 1C:
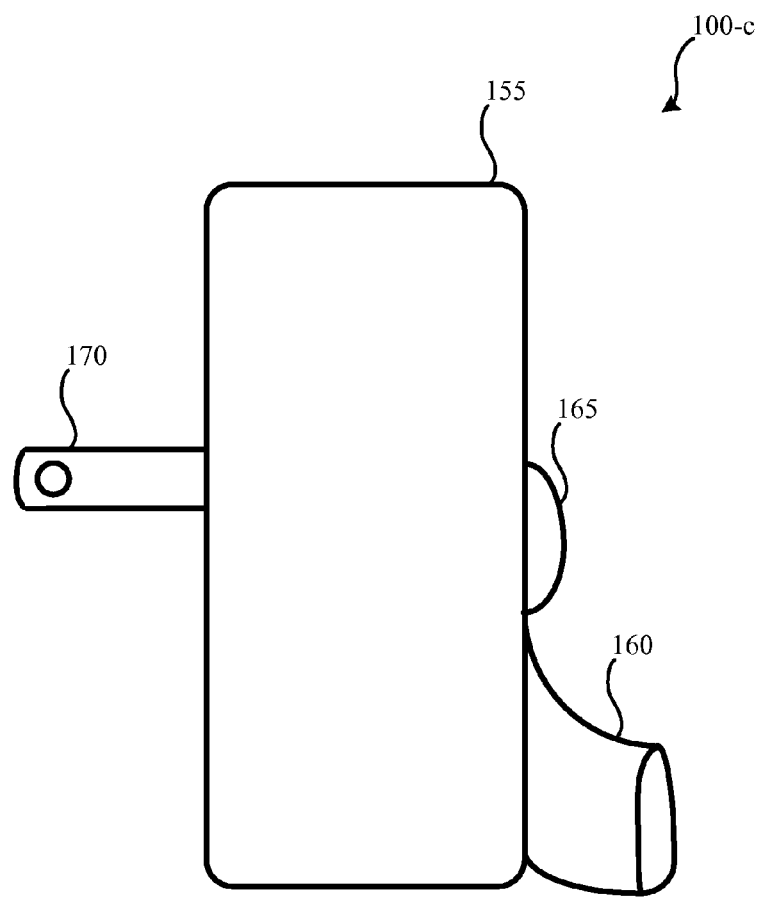
FIG. 1C illustrates a simplified embodiment of a handheld, nebulizer with an integrated driver unit.
Figure 1D:
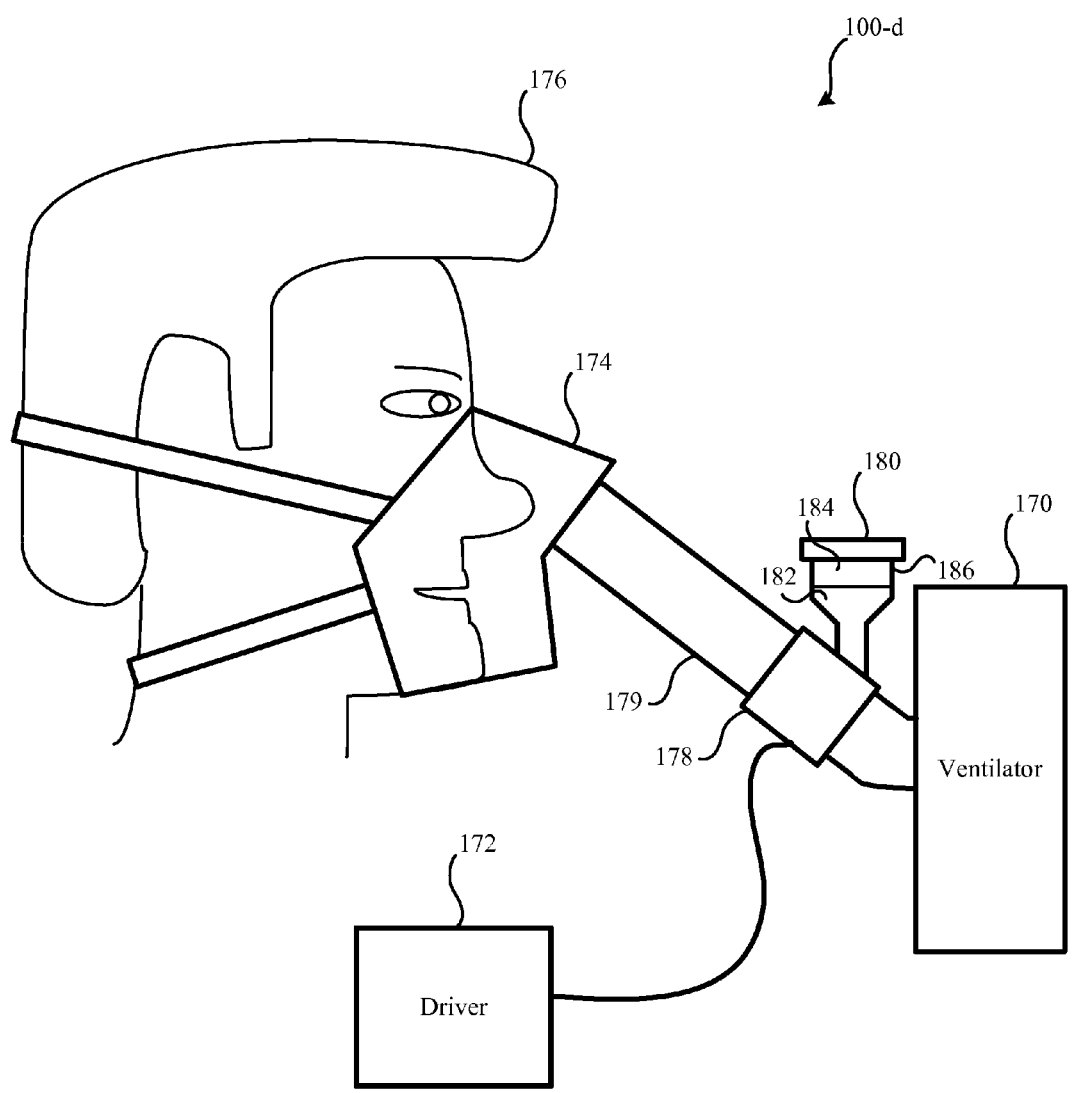
FIG. 1D illustrates a nebulizer integrated with a ventilator.

In some other embodiments of nebulizers, a driver may be incorporated into a handheld unit with the nebulizer. Nebulizer 100-c of FIG. 1C illustrates an embodiment of a handheld nebulizer with an integrated driver. Nebulizer 100-c may include a case 155, a mouthpiece 160, a trigger button 165, and an electrical plug 170. Case 155 may contain some or all of the elements found brother embodiments of nebulizers (such as nebulizer 100-a of FIG. 1A) and drivers (such as driver 152 of FIG. 1B). Therefore, contained within case 155 may be a sealed drug reservoir and/or a device capable of generating an electrical signal at a voltage magnitude and frequency to vibrate an element that atomizes liquid stored in the drug reservoir. A person receiving the atomized liquid drug may place her mouth on mouthpiece 160 and breath in. While the person receiving the atomized liquid drug is breathing in, she may press trigger button 165 to trigger the element to begin aerosolizing liquid. In some embodiments, nebulizer 100-c may contain a sensor that detects when the person is breathing in and triggers the element to vibrate without trigger button 165 being necessary.

Nebulizer 100-c may also include an electrical plug 170. Electrical plug 179 may be connected to an electrical outlet to power nebulizer 100-c. Nebulizer 100-c may contain a battery, thereby allowing electrical plug 170 to be connected to an electrical outlet when nebulizer 100-c is not in use by a person, allowing a battery to be charged. Alternatively, in some embodiments of nebulizer 100-c, electrical plug 170 may need to be connected to an electrical outlet while nebulizer 100-c is in use by a person. In some embodiments, nebulizer 100-c may use replaceable batteries as its power source.

In some embodiments, a nebulizer may operate in conjunction with a ventilator. System 100-d illustrates a nebulizer 178 that supplies atomized liquid drug to a person 176 via a ventilator 170. Ventilator 170 may supply air suitable for breathing to person 176. Ventilator 170 may assist person 176 in breathing by forcing air into the lungs of person 176 and then releasing air to mimic breathing. While person 176 is using ventilator 170, it may be necessary to provide person 176 with atomized liquid, such as a liquid drug.

Nebulizer 178 may be connected to a drug reservoir 186 that is sealed by a cap 180. Drug reservoir 186 may contain an amount of liquid drug 182. This liquid drug may be delivered to nebulizer 178 as liquid drug is atomized by nebulizer 178. As liquid drug is atomized, liquid drug 182 may drain from drug/reservoir 186, thereby increasing the volume of headspace 184. Headspace 184 may contain air. Headspace 184 may increase in volume, but may decrease in pressure as liquid drug 182 drains because liquid reservoir 186 allows no or minimal air into headspace 184.

Driver 172, which may represent the same driver as driver 152 of FIG. 1B (or may represent some other driver) may deliver a signal to nebulizer 178. This signal may control the vibration of an element of nebulizer 178. Nebulizer 178 may be attached to a tube 179 used to deliver air and atomized liquid drug to patient 176. Tube 179 may terminate in a mask 174 covering the mouth and/or nose of person 176. The air and atomized liquid drug may then enter the airways of person 176.

A nebulizer such as those illustrated in FIGS. 1A-1D may be-connected with a driver such as illustrated in FIG. 2. FIG. 2 illustrates a simplified block diagram of a nebulizer driver unit 200. The nebulizer 260 may be the nebulizer 100-*a* of FIG. 1A or it may be some other nebulizer such as those in the referenced applications or FIGS. 1B-1D. The nebulizer may be connected to the driver via a cable 270. Driver 210 may be driver 151 of FIG. 1B, or may be some other driver. Cable 270 may allow driver 210 to transmit an electrical waveform signal of varying frequency and magnitude (of voltage) through cable 270 to drive nebulizer 260.

Driver 210 may include an amplifier 230, a current phase shift detector 240, a resonant frequency tracker 220, and a voltage profile 250. Based upon the phase shift between the current supplied to nebulizer 260 and the voltage generated by amplifier 230, the nebulizer element's resonant frequency may be determined. From the resonant frequency, the negative bias pressure within the drug reservoir of the nebulizer may be determined, and the frequency and/or magnitude of the electrical waveform signal driving nebulizer 260 may be adjusted.

The determination of the resonant frequency may be accomplished using current phase shift detector 240. Current phase shift detector 240 monitors the phase shift between the phase of the current output by amplifier 230 to nebulizer 260 and the phase of the voltage output by amplifier 230 to nebulizer 260. Based upon the phase shift between the voltage and current observed by current phase shift detector 240, resonant frequency tracker 220 outputs an output waveform to amplifier 230 such that amplifier 230 outputs an electrical waveform signal with constant or near constant phase shift between the voltage and current of the electrical waveform signal driving the element of nebulizer 260.

As liquid is atomized and the bias pressure in the drug reservoir changes, the resonant frequency may change. Further, factors besides the bias pressure within the sealed drug reservoir of the nebulizer 260 may change the nebulizer element's resonant frequency. For example, the temperature of the nebulizer element, excess liquid on the nebulizer element, and or damage to the nebulizer element may cause a variation in the nebulizer element's resonant frequency. However, it may be generally accepted that during operation, changes in the nebulizer element's resonant frequency is generally due to variations in the bias pressure within the drug reservoir of the nebulizer.

The resonant frequency and/or the measured change in resonant frequency may be transmitted to voltage profile 250 by resonant frequency tracker 220. Voltage profile 250 may be used to determine the proper magnitude of voltage to apply to the nebulizer element at a particular resonant frequency to maintain consistent droplet size and dosing of the atomized liquid. In some embodiments, voltage profile 250 may include a table of empirically gathered data. In such embodiments, the resonant frequency may be located in the table, with a corresponding analog or digital signal being output to amplifier 230 that specifies the appropriate magnitude of voltage amplifier 230 should output. For example, a table may include a predetermined voltage magnitude that may be communicated to amplifier 230 when a particular resonant frequency is measured by resonant frequency tracker module 220. Voltage profile 250 may also be expressed as a graph of values, with the x-axis being frequency of the waveform generated by resonant frequency tracker 220, and the y-axis representing the appropriate voltage magnitude to be supplied to amplifier 230 such that amplifier 230 outputs an electrical signal of correct magnitude.

A rough description of one set of possible values for voltage profile 250 is that as the resonant frequency of the nebulizer element increases, the desired amplitude of the electrical signal output to the nebulizer will decrease. At a certain threshold, as the resonant frequency continues to increase, the voltage will be held by voltage profile 250 at a minimum level. In some embodiments of voltage profile 250, the signal output to amplifier 230 are determined based on a calculation using the resonant frequency supplied by resonant frequency tracker 220.

The voltage profile may need to be modified or adjusted to accommodate the characteristics (such as surface tension) of different liquids within the drug reservoir of the nebulizer. In some embodiments, a liquid drug, such as Amikasin, is used. In other embodiments, a different liquid drug or liquid is used. In some embodiments, the voltage profiles necessary for a number of liquids or liquid drugs may be similar enough that only one voltage profile needs to be used for multiple liquids or liquid drugs. Modifying or replacing voltage profile 250 may involve selecting a different liquid via a user interface on driver 210 or loading different software, firmware, and/or hardware into driver 210.

Resonant frequency tracker 220 may transmit a waveform at or near the nebulizer element's current determined resonant frequency to amplifier 230. Voltage profile 250 may transmit a signal indicating the desired voltage amplitude to be output by amplifier 230 to amplifier 230. This signal from voltage profile 250 may serve to control the gain of the amplifier 230. Based upon the input waveform from resonant frequency tracker 220 and the desired voltage amplitude received from voltage profile 250, amplifier 230 generates an output electrical signal that may be used to drive an aperture of the nebulizer. Amplifier 230 may be a variable gain linear power amplifier. In some embodiments, a fixed gain power amplifier may be used in conjunction with a variable gain amplifier or a potentiometer. Further, various other amplifiers or amplifier based circuits may be used to generate the output electrical signal to drive nebulizer 260.

Current phase shift detector 240 may create a feedback loop to resonant frequency tracker 220. Current phase shift detector 240 may determine the phase shift of the current being output from the amplifier 230. Such a phase shift may be transmitted to resonant frequency tracker 220, thereby allowing resonant frequency tracker 220 to either maintain the same frequency signal (if the phase has not shifted), increase the frequency, or decrease the frequency of the output signal in response to the resonant frequency of the nebulizer element changing as the bias pressure within the seal drug reservoir changes. Feedback through current phase shift, detector 240 may allow driver 210 to periodically or continually adjust the magnitude and frequency of the electrical signal, output to the nebulizer element while liquid is being atomized. This may allow for any change in the bias pressure in the liquid reservoir to be continually adjusted for by the driver.

Figure 2:
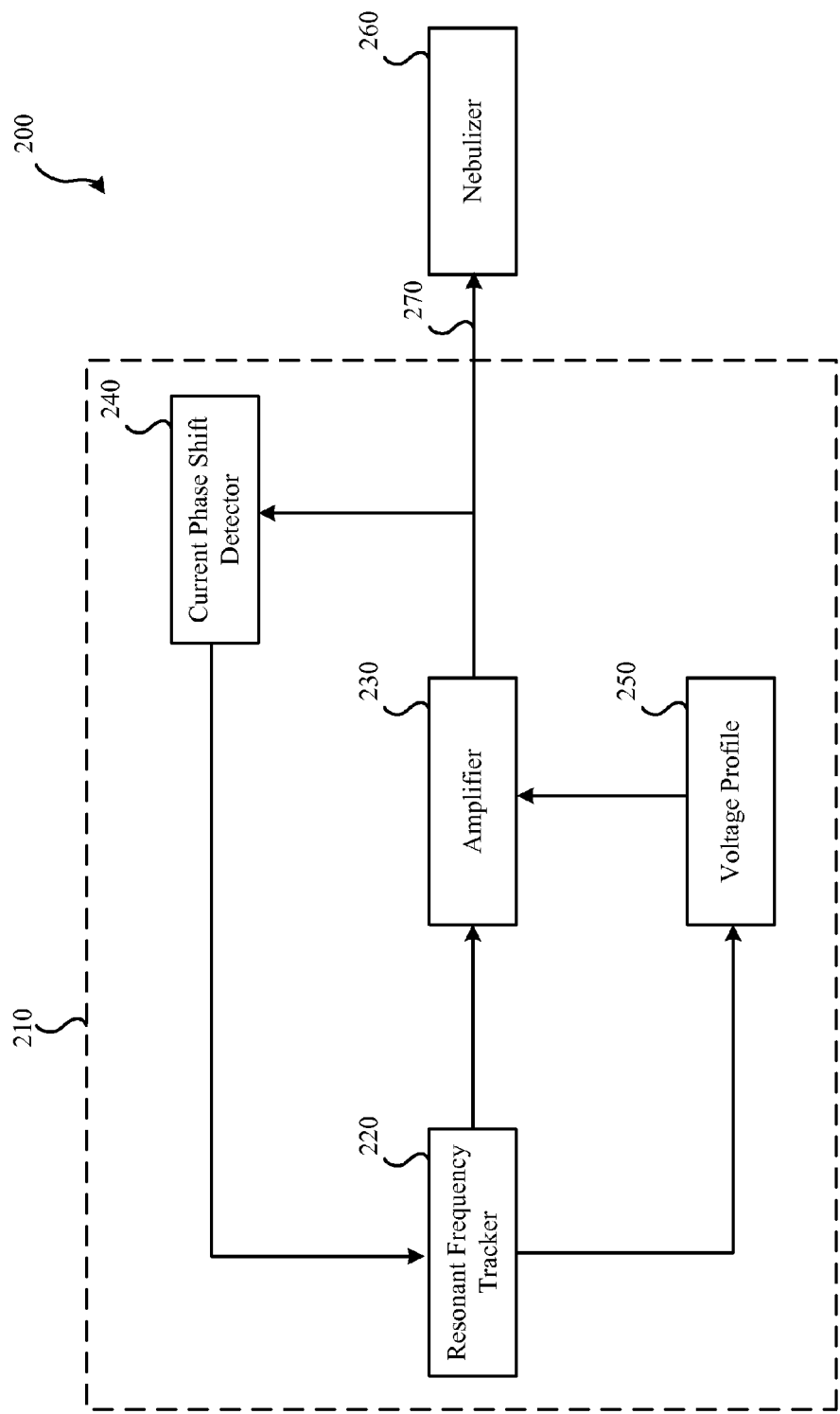
FIG. 2 illustrates a simplified embodiment of a driver coupled with a nebulizer.
Figure 3:
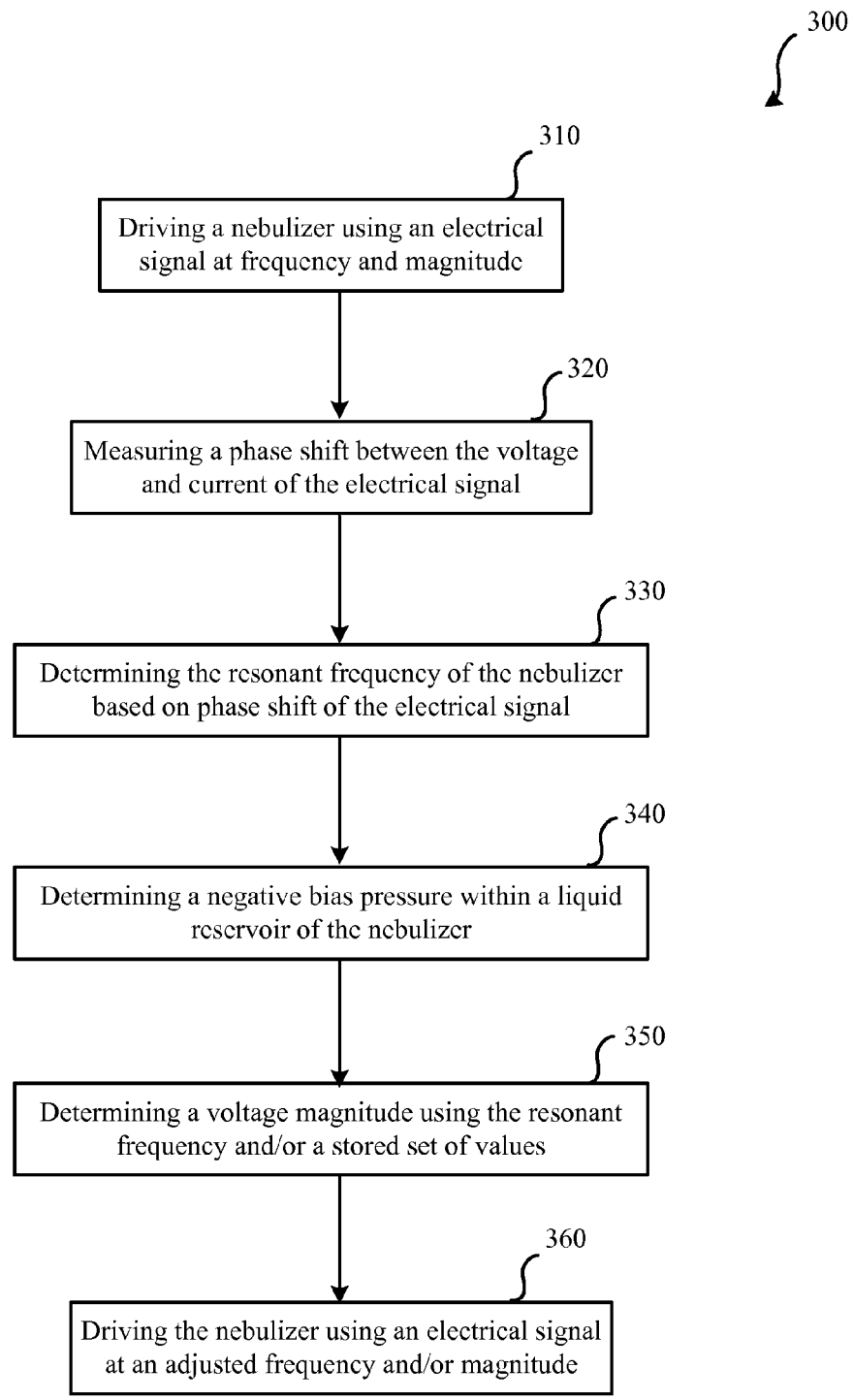
FIG. 3 illustrates a method of driving a nebulizer with a driver.

A driver, such as driver 210 of FIG. 2, may drive a nebulizer element according to a method, such as method 300 of FIG. 3. Alternatively, method 300 may be performed using some other driver. Method 300 may employ various different nebulizers, such as the nebulizers of FIGS. 1A-1D, and FIG. 2. At block 310, the driver may drive an element (also referred to as an aperture) of a nebulizer with an electrical signal. This electrical signal may be a waveform at a particular frequency and magnitude.

At block 320, the phase shift between the voltage of the electrical signal output to the nebulizer and the current of the electrical signal may be measured. Using this phase shift, at block 330, the resonant frequency of the nebulizer element may be determined. As previously noted, this resonant frequency may shift as the negative bias pressure within the liquid reservoir of the nebulizer changes. From the resonant frequency, the bias pressure within the liquid reservoir may be determined at block 340. In some embodiments, the negative bias pressure is not determined.

At block 350, the magnitude of the voltage of the electrical signal used to drive the nebulizer element may be determined. The magnitude may be determined using the resonant frequency determined at block 330 and/or the negative bias pressure determined at block 340. The resonant frequency and/or the negative bias pressure may be used to consult a table of values. This table of values may specify the appropriate magnitude of voltage to be used for the electrical signal driving the nebulizer element. Alternatively, the resonant frequency and/or the negative bias pressure may be used to calculate the appropriate voltage magnitude to drive the nebulizer element. The appropriate magnitude may correspond to a magnitude that maintains a constant dosage rate and droplet size of the liquid being dispensed from the nebulizer. The calculations or table may vary depending on the properties of the liquid being dispensed.

At block 360, the electrical waveform signal driving the nebulizer element may be adjusted according to the frequency determined at block 330 and/or the magnitude determined at block 350. If the resonant frequency of the nebulizer element has not changed, the frequency and/or the magnitude of the electrical signal driving the nebulizer element may not change. Method 300 may repeat as long as the nebulizer element is being driven by the driver.

Figure 4:
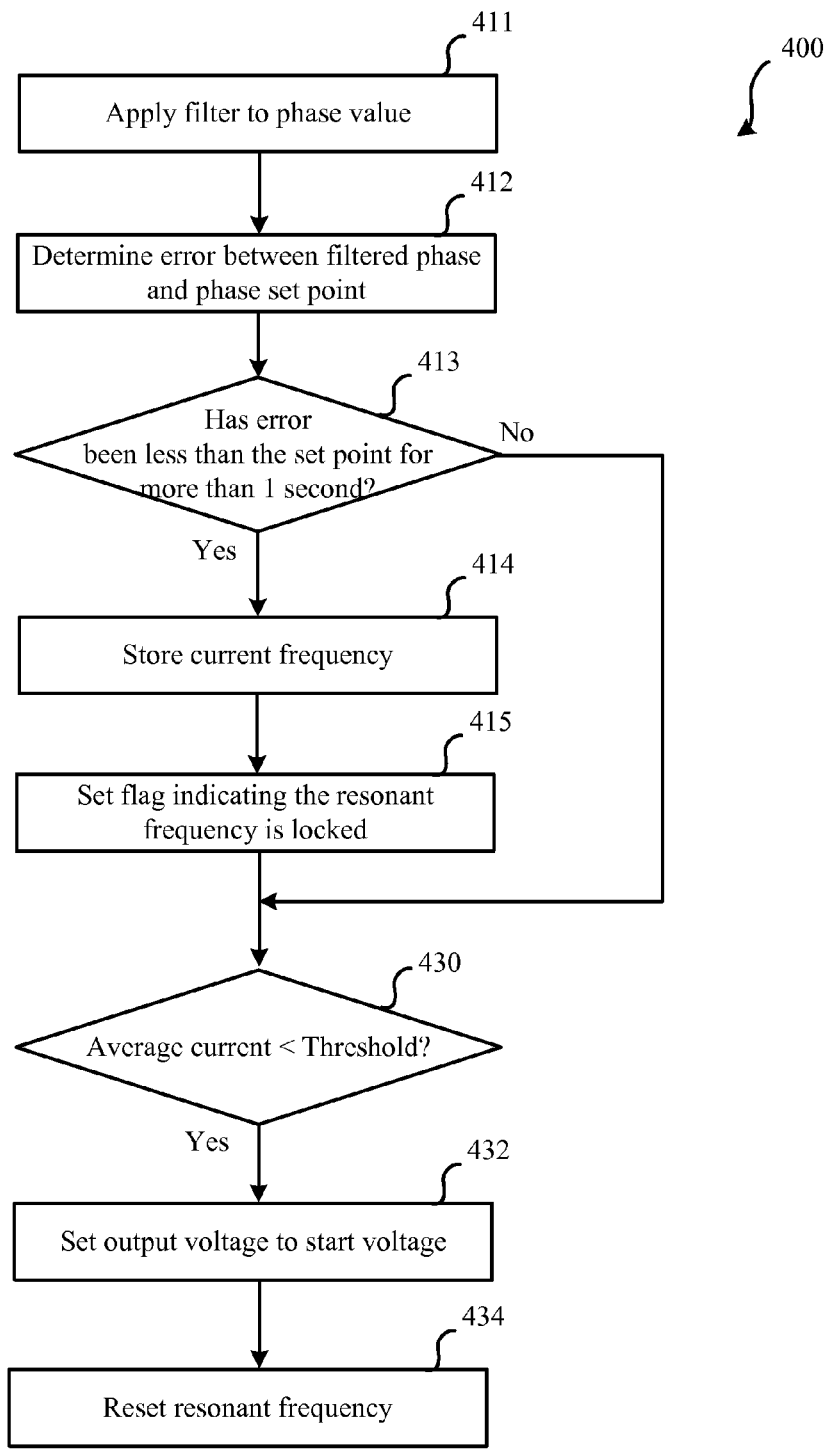
FIG. 4 illustrates a method of initially determining a resonant frequency of a nebulizer element.
Figure 5:
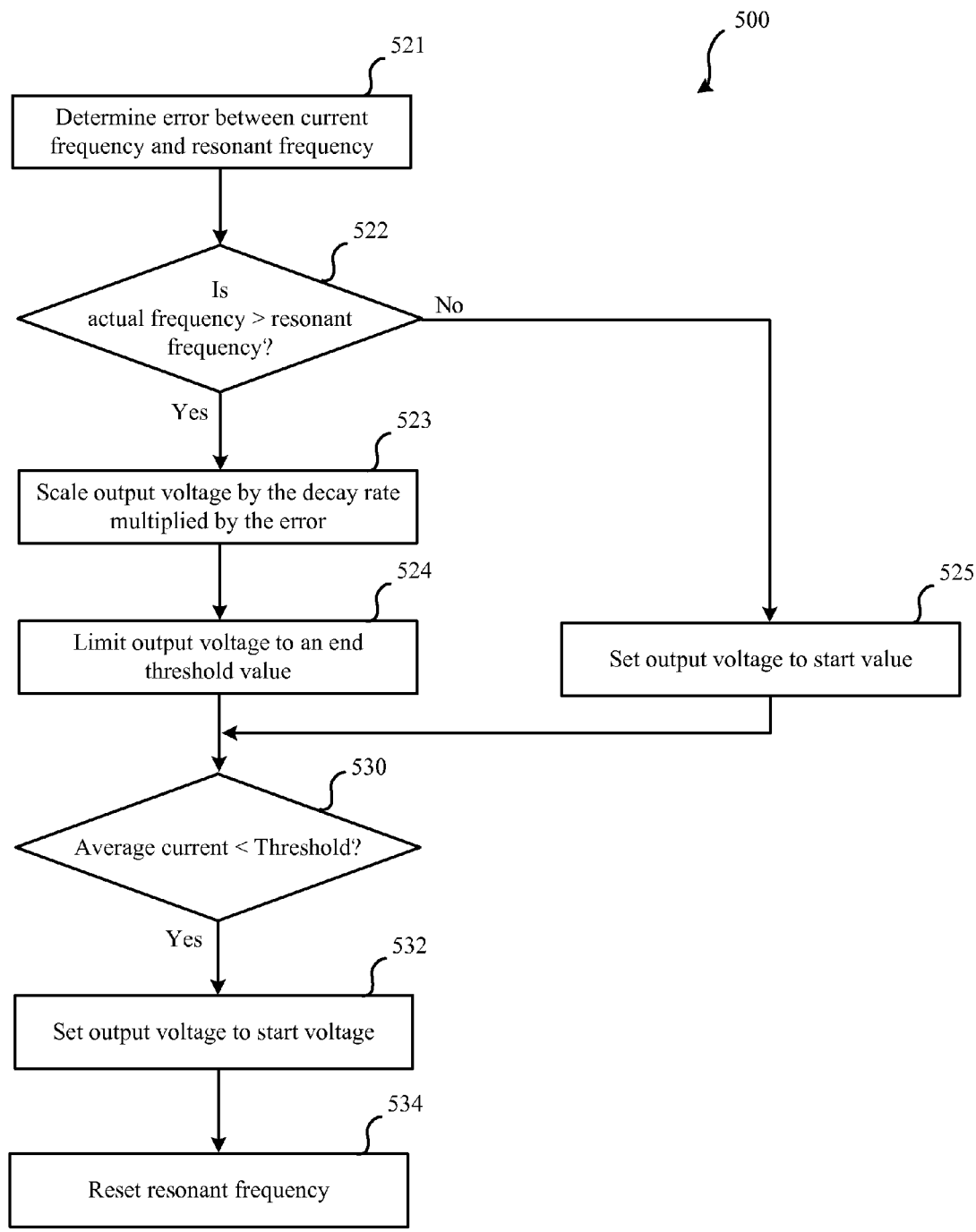
FIG. 5 illustrates a simplified method of adjusting the frequency output by a driver using a resonant frequency tracker to maintain the nebulizer element vibrating at its current resonant frequency

A resonant frequency tracker, such as resonant frequency tracker 220 of FIG. 2, may follow various methods to determine and maintain an output at or near the resonant frequency of a nebulizer element, such as nebulizer element 260 of FIG. 2. FIG. 4 illustrates a simplified flowchart of a decay profile 400 for initially determining the resonant frequency of the nebulizer element and adjusting the output electrical signal driving the nebulizer element based on the phase shift between the voltage and current of the electrical signal driving the nebulizer element detected by the current phase shift detector. Method 300 of FIG. 3 may be implemented using resonant frequency tracker 220 of FIG. 2, or may be implemented using some other resonant frequency tracker, be it implemented in software, firmware, and/or hardware.

If the resonant frequency has not been determined or "locked on" to by a resonant frequency tracker, a resonant frequency tracker may conduct method 400. The resonant frequency tracker may not have locked on to the resonant frequency if, for example, the driver has just been turned on or activated, a new nebulizer is attached to the driver unit, the nebulizer element has been interfered with, or the nebulizer element has been damaged.

At block 411, the resonant frequency tracker may apply an infinite impulse response filter ("IIR filter"), to the phase signal received from the current phase shift detector. The IIR filter may be implemented using analog and/or digital components. From this, a filtered phase value may be obtained.

Using the filter phase value, the error between the filtered phase and desired phase setpoint may be determined at block 412. The desired phase set point may indicate the phase necessary to cause the nebulizer element to vibrate at a resonant frequency. This determined error value may then be used to determine if the error has been a smaller value than the set point for greater than a second at block 413. In some embodiments, a different length of time is used.

If the error has been less than the set point for more than one second, the current frequency of the signal output to the nebulizer is stored at block 414. Further, a flag may be set to indicate that the resonant frequency has been locked on to by the resonant frequency tracker at block 415. Returning to block 413, if the error has not been less than the set point for more than one second, the process proceeds to block 430.

At block 430, if the average current is less than some threshold current value, the output voltage may be set to a start/voltage at block 432. At block 434, the resonant frequency determined by the resonant frequency tracker may be reset to an initial value. If the average current is not less than a threshold current value, blocks 432 and 434 may not be performed. Method 400 may repeat until the flag indicating the resonant frequency of the nebulizer element has been locked on to.

Once the resonant frequency has been determined and locked, which may involve the resonant frequency flag of block 414 being set, a second method may be followed. Method 500 represents a method for adjusting the frequency using a resonant frequency tracker to maintain the nebulizer element vibrating at its current resonant frequency. The error between the current frequency and resonant frequency may be determined at block 521. From this, an error value may be obtained.

A determination of whether the actual frequency of the signal being generated by the resonant frequency tracker is greater than the resonant frequency of the nebulizer element may be made at block 522. If yes, at block 523, the output voltage may be scaled by a decay rate multiplied by the error rate determined at block 521, and the output voltage may be limited to the end voltage at block 524. This may prevent the output voltage from exceeding some maximum and/or minimum threshold value. Next, the process proceeds to block 530. If the actual frequency is not determined to be greater than the resonant frequency at block 522, the output voltage is set to a start voltage at block 525, and the method proceeds to block 530.

At block 530, a determination is made if the current is less than a threshold current value. If so, the output voltage is set to the start voltage at block 532 and the resonant frequency is reset at block 534.

While a wide variety of drugs, liquids, liquid drugs, and drugs dissolved in liquid maybe aerosolized, the following provides extensive examples of what may be aerosolized. Additional examples are provided in U.S. application Ser. No. 12/341,780, the entire disclosure of which is incorporated herein for all purposes. Nearly any anti-gram-negative, anti-gram-positive antibiotic, or combinations thereof may be used. Additionally, antibiotics may comprise those having broad spectrum effectiveness, or mixed spectrum effectiveness. Antifungals, such as polyene materials, in particular, amphotericin B are also suitable for use herein. Examples of anti-gram-negative antibiotics or salts thereof include, but are not limited to, aminoglycosides or salts thereof. Examples of aminoglycosides or salts thereof include gentamicin, amikacin, kanamycin, streptomycin, neomycin, netilmicin, paramecin, tobramycin, salts thereof, and combinations thereof. For instance, gentamicin sulfate is the sulfate salt, or a mixture of such salts, of the antibiotic substances produced by the growth of *Micromonospora purpurea*. Gentamicin sulfate, USP, may be obtained from Fujian Fukang Pharmaceutical Co., LTD, Fuzhou, China. Amikacin is typically supplied as a sulfate salt, and can he obtained, for example, from Bristol-Myers Squibb. Amikacin may include related substances such as kanamicin.

Examples of anti-gram-positive antibiotics or salts thereof include, but are not limited to, macrolides or salts thereof. Examples of macrolides or salts thereof include, but are not limited to, vancomycin, erythromycin, clarithromycin, azithromycin, salts thereof, and combinations thereof. For instance, vancomycin hydrochloride is a hydrochloride salt of vancomycin, an antibiotic produced by certain strains of *Amycolatopsis orientalis*, previously designated *Streptomyces orientalis*. Vancomycin hydrochloride is a mixture of related substances consisting principally of the monohydrochloride of vancomycin B. Like all glycopeptide antibiotics, vancomycin hydrochloride contains a central core heptapeptide. Vancomycin hydrochloride, USP, may be obtained from Alpharma, Copenhagen, Denmark.

In some embodiments, the composition comprises an antibiotic and one or more additional active agents. The additional active agent described herein includes an agent, drug, or compound, which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized or systemic effect in a patient. An active agent for incorporation in the pharmaceutical formulation described herein may be an inorganic or an organic compound, including, without limitation, drugs which act on: the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system.

Examples of additional active agents include, but are not limited to, anti-inflammatory agents, bronchodilators, and combinations thereof.

Examples of bronchodilators include, but are not limited to, .beta.-agonists, anti-muscarinic agents, steroids, and combinations thereof. For instance, the steroid may comprise albuterol, such as albuterol sulfate.

Active agents may comprise, for example, hypnotics and sedatives, psychic energizers, tranquilizers, respiratory drugs, anticonvulsants, muscle relaxants, antiparkinson agents (dopamine antagnonists), analgesics, anti-inflammatories, antianxiety drugs (anxiolytics), appetite suppressants, antimigraine agents, muscle contractants, additional anti-infectives (antivirals, antifungals, vaccines) antiarthritics, antimalarials, antiemetics, anepileptics, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents. The active agent, when administered by inhalation, may act locally or systemically.

The active agent may fall into one of a number of structural classes, including but not limited to small molecules, peptides, polypeptides, proteins, polysaccharides, steroids, proteins capable of eliciting physiological effects, nucleotides, oligonucleotides, polynucleotides, fats, electrolytes, and the like, Examples of active agents suitable for use in this invention include but are not limited to one or more of calcitonin, amphotericin B, erythropoietin (EPO), Factor VIII, Factor IX, ceredase, cerezyme, cyclosporin, granulocyte colony stimulating factor (GCSF), thrombopoietin (TPO), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-1 receptor, interleukin-2, interleukin-1 receptor antagonist, interleukin-3, interleukin-4, interleukin-6, luteinizing hormone releasing hormone (LHRH), factor IX, insulin, pro-insulin, insulin analogues (e.g., mono-acylated insulin as described in U.S. Pat. No. 5,922,675, which is incorporated herein by reference in its entirety), amylin, C-peptide, somatostatin, somatostatin analogs including octreotide, vasopressin, follicle stimulating hormone (FSH), insulin-like growth factor (IGF), insulintropin, macrophage colony stimulating factor (M-CSF), nerve growth factor (NGF), tissue growth factors, keratinocyte growth factor (KGF), glial growth factor (GGF), tumor necrosis factor (TNF), endothelial growth factors, parathyroid hormone (PTH), glucagon-like peptide thymosin alpha 1, IIb/IIIa inhibitor, alpha-1 antitrypsin, phosphodiesterase (PDE) compounds, VLA-4 inhibitors, bisphosphonates, respiratory syncytial virus antibody, cystic fibrosis transmembrane regulator (CFTR) gene, deoxyreibonuclease (Dnase), bactericidal/permeability increasing protein (BPI), anti-CMV antibody, 1 3-cis retinoic acid, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin, teicoplanin, rampolanin, mideplanin, colistin, daptomycin, gramicidin, colistimethate, polymixins such as polymixin B, capreomycin, bacitracin, penems; penicillins including penicllinase-sensitive agents like penicillin G, penicillin V, penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, lidocaine, metaproterenol sulfate, beclomethasone diprepionate, triamcinolone acetamide, budesonide acetonide, fluticasone, ipratropium bromide, flunisolide, cromolyn sodium, ergotamine tartrate and where applicable, analogues, agonists, antagonists, inhibitors, and pharmaceutically acceptable salt forms of the above. In reference to peptides and proteins, the invention is intended to encompass synthetic, native, glycosylated, unglycosylated, pegylated forms, and biologically active fragments, derivatives, and analogs thereof.

Active agents for use in the invention further include nucleic acids, as bare nucleic acid molecules, vectors, associated viral particles, plasmid DNA or RNA or other nucleic acid constructions of a type suitable for transfection or transformation of cells, i.e., suitable for gene therapy including antisense. Further, an active agent may comprise live attenuated or killed viruses suitable for use as vaccines. Other useful drugs include those listed within the Physician's Desk Reference (most recent edition), which is incorporated herein by reference in its entirety.

The amount of antibiotic or other active agent in the pharmaceutical formulation will be that amount necessary to deliver a therapeutically or prophylactically effective amount of the active agent per unit dose to achieve the desired result. In practice, this will vary widely depending upon the particular agent, its activity, the severity of the condition to be treated, the patient population, dosing requirements, and the desired therapeutic effect. The composition will generally contain anywhere from about 1 wt % to about 99 wt %, such as from about 2 wt % to about 95 wt %, or from about 5 wt % to 85 wt %, of the active agent, and will also depend upon the relative amounts of additives contained in the composition. The compositions of the invention are particularly useful for active agents that are delivered in doses of from 0.001 mg/day to 100 mg/day, such as in doses from 0.01 mg/day to 75 mg/day, or in doses from 0.10 mg/day to 50 mg/day. It is to be understood that more than one active agent may be incorporated into the formulations described herein and that the use of the term "agent" in no way excludes the use of two or more such agents.

Generally, the compositions are free of excessive excipients. In one or more embodiments, the aqueous composition consists essentially of the anti-gram-negative antibiotic, such as amikacin, or gentamicin or both, and/or salts thereof and water.

Further, in one or more embodiments, the aqueous composition is preservative-free. In this regard, the aqueous composition may be methylparaben-free and/or propylparaben-free. Still further, the aqueous composition may be saline-free.

In one or more embodiments, the compositions comprise an anti-infective and an excipient. The compositions may comprise a pharmaceutically acceptable excipient or carrier which may be taken into the lungs with no significant adverse toxicological effects to the subject, and particularly to the lungs of the subject. In addition to the active agent, a pharmaceutical formulation may optionally include one or more pharmaceutical excipients which are suitable for pulmonary administration. These excipients, if present, are generally present in the composition in amounts sufficient to perform their intended function, such as stability, surface modification, enhancing effectiveness or delivery of the composition or the like. Thus if present, excipient may range from about 0.01 wt % to about 95 wt %, such as from about 0.5 wt % to about 80 wt %, from about 1 wt % to about 60 wt %. Preferably, such excipients will, in part, serve to further improve the features of the active agent composition, for example by providing more efficient and reproducible delivery of the active agent, and/or facilitating manufacturing. One or more excipients may also be provided to serve as bulking agents when it is desired to reduce the concentration of active agent in the formulation.

For instance, the compositions may include one or more osmolality adjuster, such as sodium chloride. For instance, sodium chloride may be added to solutions of vancomycin hydrochloride to adjust the osmolality of the solution. In one or more embodiments, an aqueous composition consists essentially of the anti-gram-positive antibiotic, such as vancomycin hydrochloride, the osmolality adjuster, and water.

Pharmaceutical excipients and additives useful in the present pharmaceutical formulation include but are not limited to amino acids, peptides, proteins, non-biological polymers, biological polymers, carbohydrates, such as sugars, derivatized sugars such as alditols, aldonic acids, esterified sugars, and sugar polymers, which may be present singly or in combination.

Exemplary protein excipients include albumins such as human serum, albumin (HSA), recombinant human albumin (rHA), gelatin, casein, hemoglobin, and the like. Suitable amino acids (outside of the dileucyl-peptides of the invention), which may also function in a buffering capacity, include alanine, glycine, arginine, betaine, histidine, glutamic acid, aspartic acid, cysteine, lysine, leucine, isoleucine, valine, methionine, phenylalanine, aspartame, tyrosine, tryptophan, and the like. Preferred are amino acids and polypeptides that function as dispersing agents. Amino acids falling into this category include hydrophobic amino acids such as leucine, valine, isoleucine, tryptophan, alanine, methionine, phenylalanine, tyrosine, histidine, and proline.

Carbohydrate excipients suitable for use in the invention include, for example, monosaccharides such as fructose, maltose, galactose, glucose, D-marmose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), pyranosyl sorbitol, myoinositol and the like.

The pharmaceutical formulation may also comprise a buffer or a pH adjusting agent, typically a salt prepared from an organic acid or base. Representative buffers comprise organic acid salts of citric acid, ascorbic acid, gluconic acid, carbonic acid, tartaric acid, succinic acid, acetic acid, or phthalic acid, Tris, tromethamine hydrochloride, or phosphate buffers.

The pharmaceutical formulation may also include polymeric excipients/additives, e.g., polyvinylpyrrolidones, celluloses and derivatized celluloses such, as hydroxymethylcellulose, hydroxyethylcellulose, and hydroxypropylmethylcellulose, Ficolls (a polymeric sugar), hydroxyethylstarch, dextrates (e.g., cyclodextrins, such as 2-hydroxypropyl-.beta.-cyclodextrin and sulfobutylether-.beta.-cyclodextrin), polyethylene glycols, and pectin.

The pharmaceutical formulation may further include flavoring agents, taste-masking agents, inorganic salts (for example sodium chloride), antimicrobial agents (for example benzalkonium chloride), sweeteners, antioxidants, antistatic agents, surfactants (for example polysorbates such as "TWEEN 20" and "TWEEN 80"), sorbitan esters, lipids (for example phospholipids such, as lecithin and other phosphatidylcholines, phosphatidylethanolamines), fatty acids and fatty esters, steroids (for example cholesterol), and chelating agents (for example EDTA, zinc and other such suitable cations). Other pharmaceutical excipients and/or additives suitable for use in the compositions according to the invention are listed in "Remington: The Science & Practice of Pharmacy", 19.sup.th ed., Williams & Williams, (1995), and in the "Physician's Desk Reference", 52.sup.nd ed., Medical Economics, Montvale, N.J. (1998), both of which are incorporated herein by reference in their entireties.

It should be noted that the methods, systems, and devices discussed above are intended merely to be examples. It must be stressed-that various embodiments may omit, substitute, or add various procedures or components as appropriate. For instance, it should be appreciated that, in alternative embodiments, the methods may be performed in an order different from that described, and that various steps may be added, omitted, or combined. Also, features described with respect to certain embodiments may be combined in various other embodiments. Different aspects and elements of the-embodiments, may be combined in a similar manner. Also, it should be emphasized that technology evolves and, thus, many of the elements are examples and should not be interpreted to limit the scope of the invention.

Specific details are given in the description to provide a thorough understanding of the embodiments. However, it will be understood by one of ordinary skill in the art that the embodiments may be practiced without these specific details. For example, well-known processes, algorithms, structures, and techniques have been shown without unnecessary detail in order to avoid obscuring the embodiments. This description provides example embodiments only, and is not intended to limit the scope, applicability, or configuration of the invention. Rather, the preceding description of the embodiments will provide those skilled in the art with an enabling description for implementing embodiments of the invention. Various changes may be made in the function and arrangement of elements without departing from the spirit and scope of the invention.

Further, the preceding description generally details aerosolizing liquid drugs. However, it should be understood that liquids besides liquid drugs may be aerosolized using similar devices and methods.

Also, it is noted that the embodiments may be described as a process which is depicted as a flow diagram or block diagram. Although each may describe the operations as a sequential process, many of the operations can be performed in parallel or concurrently. In addition, the order of the operations may be rearranged. A process may have additional steps not included in the figure.

What is claimed is:

1. A method for determining a resonant frequency of an element of a nebulizer with a negatively biased liquid reservoir, the method comprising:
    driving, by a driver, the element of the nebulizer using an electrical signal to atomize a liquid, the electrical signal comprising a current and a voltage;
    measuring, by the driver, a phase shift between the voltage and the current of the electrical signal driving the nebulizer;

based at least in part on the phase shift of the electrical signal driving the element of the nebulizer measured by the driver, determining, by the driver, a resonant frequency of the element of the nebulizer;

determining, by the driver, a voltage magnitude for the electrical signal based on the determined resonant frequency of the nebulizer and a stored voltage profile based on characteristics of the type of liquid being atomized; and causing, by an amplifier of the driver, the electrical signal driving the nebulizer to have the determined voltage magnitude.

2. The method of claim 1, wherein the negatively biased liquid reservoir causes the resonant frequency of the element of the nebulizer to vary as liquid is drained from the negatively biased liquid reservoir.

3. The method of claim 1, wherein the electrical signal driving the nebulizer causes the element of the nebulizer to vibrate and atomize liquid stored in the negatively biased liquid reservoir.

4. The method of claim 1, further comprising, based at least in part on the resonant frequency of the nebulizer determined by the driver, determining, by the driver, a negative bias pressure within the negatively biased liquid reservoir of the nebulizer.

5. The method of claim 1, further comprising, adjusting, by the driver, the frequency of the electrical signal to the nebulizer, wherein a roughly constant phase shift is maintained between the voltage and current of the electrical signal.

6. The method of claim 2, wherein the voltage magnitude is determined using a stored set of values, and the stored set of values vary depending on the type of the liquid in the negatively biased liquid reservoir.

7. A device for driving an element of a nebulizer, the device comprising:
   an amplifier, configured to generate an output waveform signal, the output waveform signal comprising an output frequency, an output current, and an output voltage, wherein the output waveform signal drives the element of the nebulizer at the output frequency;
   a phase shift detector, configured to determine a phase shift between the output current and the output voltage of the output waveform signal;
   a resonant frequency tracker, configured to generate a waveform signal of a variable frequency that is input to the amplifier wherein the waveform signal controls the output frequency, wherein the variable frequency is adjusted based on the phase shift of the output waveform signal determined by the phase shift detector module; and
   a voltage profile, configured to adjust a magnitude of the output voltage of the output waveform signal output by the amplifier based on the frequency of the waveform signal generated by the resonant frequency tracker, the voltage profile being defined as a set of stored values based on characteristics of a type of liquid being atomized.

8. The device of claim 7, wherein the nebulizer has a negatively biased liquid reservoir that causes the resonant frequency of the element of the nebulizer to vary as liquid is drained from the negatively biased liquid reservoir.

9. The driver device of claim 8, wherein the liquid stored in the negatively biased liquid reservoir is a drug.

10. The driver device of claim 7, wherein the driver device is coupled with the nebulizer in a handheld unit.

11. A system for atomizing liquid, the system comprising:
    a liquid reservoir that is adapted to hold a liquid that is to be atomized;
    a nebulizer, comprising an element having a plurality of apertures, wherein:
      the element is configured to vibrate to atomize liquid drained from the liquid reservoir wherein the element is driven by an output waveform signal;
      a negative bias pressure of the liquid reservoir changes as liquid stored in the liquid reservoir is drained; and
      the liquid reservoir is sealed such that air from the ambient environment substantially does not enter the liquid reservoir as liquid stored in the liquid reservoir is drained; and
    a driver, comprising:
      a phase shift detector, configured to determine a phase shift between a current of the output waveform signal and a voltage of the output waveform signal;
      a resonant frequency tracker, configured to generate a waveform that adjusts the frequency of the output waveform signal, wherein the frequency is adjusted based on the phase shift determined by the phase shift detector; and
      a voltage profile, configured to adjust a magnitude of the voltage of the output waveform signal based on the frequency of the waveform generated by the resonant frequency tracker, the voltage profile being defined as a set of stored values based on characteristics of a type of liquid being atomized.

12. The system of claim 11, wherein the nebulizer is configured to be coupled with a ventilator.

13. The system of claim 11, wherein the driver is coupled with the nebulizer in a handheld unit.

14. The system of claim 11, wherein the driver further comprises an amplifier configured to generate the output waveform signal using signals from the resonant frequency tracker and the voltage profile.

15. The system of claim 11, wherein the liquid is a drug.

16. A method for aerosolizing a liquid, the method comprising:
    sealing the liquid within a reservoir;
    generating an output waveform signal;
    vibrating a nebulizer element to aerosolize the liquid, wherein:
      a negative pressure is produced within the reservoir as the liquid is aerosolized; and
      the output waveform signal causes the nebulizer element to vibrate;
    determining a phase shift between a current of the output waveform signal and a voltage of the output waveform signal;
    adjusting a frequency of the output waveform signal at least partially based on the phase shift; and
    adjusting a magnitude of the voltage of the output waveform signal at least partially based on the frequency of the output waveform signal and a stored set of values, wherein the stored set of values vary depending on a type of the liquid being aerosolized.

17. The system of claim 16, wherein the nebulizer element is coupled with a nebulizer and the nebulizer is configured to be coupled with a ventilator.

18. The method of claim 16, wherein the phase shift is generally maintained constant between the voltage and current of the output waveform signal.

19. The method of claim 16, wherein the output waveform signal causes the nebulizer element to vibrate at generally a resonant frequency of the nebulizer element.

* * * * *